United States Patent [19]

Gallagher et al.

[11] Patent Number: 5,639,008
[45] Date of Patent: Jun. 17, 1997

[54] ANVIL FOR CIRCULAR STAPLER

[75] Inventors: Richard J. Gallagher, Milford; David N. Fowler, Trumbull, both of Conn.

[73] Assignee: The United States Surgical Corporation, Norwalk, Conn.

[21] Appl. No.: 598,859

[22] Filed: Feb. 9, 1996

Related U.S. Application Data

[62] Division of Ser. No. 558,341, Nov. 15, 1995, Pat. No. 5,588,579, which is a continuation of Ser. No. 296,218, Aug. 25, 1994, abandoned.

[51] Int. Cl.$^6$ ................................................. A61B 17/068
[52] U.S. Cl. .................... 227/175.1; 227/19; 227/180.1
[58] Field of Search ............................ 227/19, 175.1, 227/176.1, 180.1

[56] References Cited

U.S. PATENT DOCUMENTS

| | | |
|---|---|---|
| 3,193,165 | 7/1965 | Akhalaya et al. . |
| 3,593,903 | 7/1971 | Astafiev et al. . |
| 4,198,982 | 4/1980 | Fortner et al. . |
| 4,304,236 | 12/1981 | Conta et al. ............................ 227/19 |
| 4,379,457 | 4/1983 | Gravener et al. . |
| 4,473,077 | 9/1984 | Noiles et al. . |
| 4,476,863 | 10/1984 | Kanshin et al. . |
| 4,505,272 | 3/1985 | Utyamyshev . |
| 4,505,414 | 3/1985 | Filipi . |
| 4,537,193 | 8/1985 | Tanner . |
| 4,566,620 | 1/1986 | Green et al. . |
| 4,573,468 | 3/1986 | Conta et al. . |
| 4,576,167 | 3/1986 | Noiles . |
| 4,603,693 | 8/1986 | Conta et al. . |
| 4,606,343 | 8/1986 | Conta et al. . |
| 4,610,383 | 9/1986 | Rothfuss et al. . |
| 4,646,745 | 3/1987 | Noiles . |
| 4,671,445 | 6/1987 | Barker et al. . |
| 4,700,703 | 10/1987 | Resnick et al. . |
| 4,784,137 | 11/1988 | Kulik et al. . |
| 4,817,847 | 4/1989 | Redtenbacher et al. . |
| 4,848,367 | 7/1989 | Avant et al. . |

(List continued on next page.)

FOREIGN PATENT DOCUMENTS

| | | |
|---|---|---|
| 1136020 | 12/1979 | Canada . |
| 0190022 | 8/1986 | European Pat. Off. . |
| 270260 | 6/1988 | European Pat. Off. . |
| 282157 | 9/1988 | European Pat. Off. . |
| 1461464 | 12/1966 | France . |
| 1588250 | 4/1970 | France . |
| 2443239 | 12/1979 | France . |
| 1057729 | 5/1959 | Germany . |
| 3301713 | 7/1984 | Germany . |
| 7711347 | 4/1979 | Netherlands . |
| 2016991 | 9/1979 | United Kingdom ................ 227/180.1 |
| 2070500 | 9/1981 | United Kingdom . |
| WO8706448 | 11/1987 | WIPO . |
| WO9006085 | 6/1990 | WIPO . |

OTHER PUBLICATIONS

European Search Report dated Apr. 16, 1996.
"Use of the Stapler in Interior Reception for Cancer of the Rectosigmoid" Resnicle et al., Israel Journal of Medical Sciences, vol. 19, 1983, pp. 128–133.
"New Method of Bowel Stoma Formation," American Journal of Surgery, vol. 152, Nov. 1986, pp. 545–548.
EEA Anvil With A Separate Short–Shaft–Non–Confidential Disclosure Agreement, Sep. 1981.
"Minimally Invasive Colon Resection (Laparoscopic Colectomy)" Jacobs et al., Surgical Laparoscopy & Endoscopy, vol. 1, No. 3, Sep. 1991, pp. 144–150.
U.S. Surgical Corporation, "Auto Suture Information Booklet" 1990.
European Search Report dated Feb. 19, 1996.

*Primary Examiner*—Scott A. Smith

[57] ABSTRACT

An anvil assembly for a surgical fastening instrument is disclosed. The anvil is constructed to pivot relative to an anvil shaft to facilitate movement of the anvil and instrument during use. The anvil also has an improved surface for severing structures and a sloped surface for guiding a knife during use.

3 Claims, 11 Drawing Sheets

U.S. PATENT DOCUMENTS

| | | |
|---|---|---|
| 4,873,977 | 10/1989 | Avant et al. . |
| 4,903,697 | 2/1990 | Resnick et al. . |
| 5,104,025 | 4/1992 | Main et al. . |
| 5,108,420 | 4/1992 | Marks . |
| 5,119,983 | 6/1992 | Green et al. . |
| 5,122,156 | 6/1992 | Green et al. . |
| 5,139,513 | 8/1992 | Segato . |
| 5,197,649 | 3/1993 | Bessler et al. . |
| 5,205,459 | 4/1993 | Brinkerhoff et al. . |
| 5,271,543 | 12/1993 | Grant et al. . |
| 5,312,024 | 5/1994 | Grant et al. ............................ 227/19 |
| 5,344,059 | 9/1994 | Green et al. . |
| 5,411,508 | 5/1995 | Bessler . |
| B1 4,319,576 | 2/1986 | Rothfuss . |

ANVIL FOR CIRCULAR STAPLER

This is a divisional of U.S. application Ser. No. 08/558,341 filed Nov. 15, 1995, now U.S. Pat. No. 5,588,579, which is a continuation of U.S. patent application Ser. No. 08/296,218 filed Aug. 25, 1994, now abandoned.

BACKGROUND

1. Technical Field

This invention relates to an anvil assembly for a surgical fastener applying instrument. More particularly, this invention relates to a pivotable anvil assembly for a circular anastomosis surgical stapling instrument

2. Background of Related Art

Various types of surgical fastener applying instruments are known for the application of surgical fasteners to tissue. A common type of surgical fastener is a surgical staple. Surgical stapling instruments typically have a mechanism for firing a plurality of staples from a staple holding cartridge and an anvil disposed opposite the staple cartridge against which the staples are formed. Such instruments include, for example, linear staplers, which typically apply one or more parallel rows of staples, and circular staplers, which typically apply one or more concentric/circular rows of staples. In use, the surgeon will place tissue between the staple cartridge and anvil and, by firing the instrument, cause the staples to become clenched to the tissue.

Circular staplers are known and have been successfully used in surgical procedures for many years. Commercially available instruments include the CEEA® circular stapler, manufactured by United States Surgical Corporation, Norwalk, Conn., and the ILS® circular stapler, manufactured by Ethicon, Inc., Blue Ash, Ohio. Various embodiments of circular staplers have been disclosed in commonly assigned U.S. Pat. Nos. 4,576,167, 4,603,693, 5,005,749, and 5,119,983. These instruments are typically indicated for use in gastric and esophageal surgery wherein tubular organs are joined to other anatomical structures.

In one common procedure, known as end-to-end anastomosis, a portion of the intestinal tract is removed (i.e., due to the presence of disease such as cancer) and the remaining ends are rejoined by using a circular stapler. To join the tubular structures, one end of intestine is secured about an anvil and the other end of intestine is held in place adjacent a staple cartridge. Preferably, the anvil has a shaft that is removably connected to the instrument. Once the anvil shaft is secured to the instrument, the anvil is drawn into close approximation to the stapling cartridge. The instrument is then fired to cause the staples to pass through tissue of both organs and become formed against the anvil. During the firing step, a circular knife is advanced to cut tissue inside the staple line, thereby establishing a passage between the organs. After firing, the instrument is typically removed by withdrawing the anvil through the staple line, after which the surgeon will carefully inspect the surgical site to ensure a proper anastomosis (joining) has been achieved.

During withdrawal of the anvil, there can be a noticeable resistance as the anvil passes by the staple line. Since the staples have been freshly placed and tissue freshly cut, minimal manipulation of the surgical sight is desired. A proposed solution to reduce removal force is found in U.S. Pat. No. 4,505,272, issued in 1985 to Utyamyshev, et al. The '272 patent discloses an anvil which breaks into four pieces after firing, and, therefore, is more easily pulled through the stapled anastomosis. Unfortunately, the construction of Utyamyshev's anvil is quite complicated and would be expensive to manufacture. Ethicon, Inc., in its ILS® circular stapler, has chosen to have the knife cut relatively close to the staple line, thereby providing a larger opening for the anvil. A disadvantage of this design, however, is that the surgical site has less tissue in the stapled area and can be more prone to leakage or rupture.

A more economical and efficacious approach to decrease resistance upon anvil removal was developed by U.S. Surgical, and is disclosed in European Patent Application No. 570,915 A2. This application discloses an anvil that pivots relative to a portion of the anvil shaft. Pivoting allows the anvil to move to a position wherein a smaller surface area of the anvil passes through the anastomotic sight, as compared to the surface area with no pivoting. While this pivoting anvil is useful, it could be improved by providing structure that permits control over the pivoting movement of the anvil relative to the shaft.

Therefore, there is a need to provide a circular stapling instrument having an anvil that is easily removed from the surgical site. This need should be satisfied without compromising the safety of the patient and, particularly in this era of "Health Care Reform", this need should be satisfied in a cost effective manner.

When performing a circular anastomosis, proper alignment of the knife and complete severance of all structures in the path of the knife blade is key to successful operation of the instrument. The difficulty of this cutting step can be dependent on the technique used by the surgeon. In so called "triple stapling" procedures, for example, the intestine ends to be joined are each initially closed by one or more lines of staples. When joining is performed with a circular stapler, one or more of these lines of staples can become disposed between the anvil and staple cartridge. In this event, during the cutting step, the knife blade can come into contact with both tissue and one or more staples. To facilitate cutting of tissue, it is well known in the art to provide plastic or other semi-rigid ring members in the path of the knife blade. See, for example, U.S. Pat. Nos. 4,289,133, 4,304,236 and 5,119,983. While these structures are effective in aiding the knife to cut tissue, staples can remain uncut and deformed after firing. Such uncut staples are undesirable.

Therefore, a need exists for circular staplers wherein the cutting knife can sever both tissue and staples during use. In addition, there is a need to ensure proper alignment of the knife with that which it is designed to contact in order to sever the tissue and staples.

SUMMARY

The present invention provides an anvil for a circular stapler which is pivotable relative to the anvil shaft. By allowing the anvil to pivot, the profile of the anvil is significantly reduced and the anvil easily passes through the staple line. In a preferred embodiment, a biasing spring is disposed between the anvil and the shaft to facilitate pivoting. Preferably, the spring is a coiled spring, however other spring-type structures can be used, such as torsion springs, leaf springs, flat springs and the like.

In another preferred embodiment, a retaining member is provided to releasably lock the anvil perpendicular to the longitudinal axis of the anvil shaft. The retaining member is preferably at least partially dispose within the anvil and movable from a first position, wherein the anvil is prevented from pivoting relative to the shaft, to a second position, wherein the anvil is pivotable relative to the shaft. Optionally, a resilient member can be disposed adjacent the retaining member to bias the retaining member into the first position. During firing, an element of the apparatus causes the retaining member to move from the first position to the second position. With the retaining member disposed in the second position, the anvil is then free to pivot relative to the shaft under the biasing force of the spring.

In another embodiment, a sloped annular surface portion is associated with the anvil to help guide the knife during firing. The annular surface portion slopes radially inwardly and distally from the anvil's staple forming surface. Upon firing of the instrument, distal movement of the knife blade from the apparatus toward the anvil causes the knife blade to approach the anvil area inside the staple forming surface. If the knife is off-center, contact with the sloped annular surface portion will direct the knife to a more desired, central orientation.

In another embodiment, an improved knife contacting surface is provided. Preferably, the knife contacting surface is disposed within the anvil and fabricated from a rigid material, such as stainless steel. A rigid knife contacting surface facilitates cutting, and is particularly useful to sever staples which may be in the path of the knife. Preferably, the anvil further has a cut ring at least partially disposed proximal of the knife contacting surface, i.e., such that the knife initially penetrates the cut ring before contacting the knife contacting surface. The cut ring can be manufactured from a semi-rigid biocompatible material such as polyethylene or polypropylene. Semi-rigid materials such as the foregoing plastics, are useful for severing tissue but not staples. In contrast, rigid materials such as stainless steel are useful for severing staples, but not for completely cutting tissue. Therefore, the combination of semi-rigid and rigid materials in the path of the knife as proposed herein is ideal for accomplishing both purposes.

In use, distal movement of the knife during firing will initially cut tissue against the semi-rigid cut ring as the knife passes through the semi-rigid cut ring and subsequently will cut staples against the rigid knife contacting surface, where upon distal movement of the knife is terminated. The knife contacting surface is preferably metal, but can also be of any other rigid material such as ceramic, hard plastic, or other man-made or natural substances with sufficient hardness.

BRIEF DESCRIPTION OF THE DRAWINGS

Various embodiments are described herein with reference to the drawings, wherein.

DETAILED DESCRIPTION OF THE PREFERRED EMBODIMENTS

Figure 1:
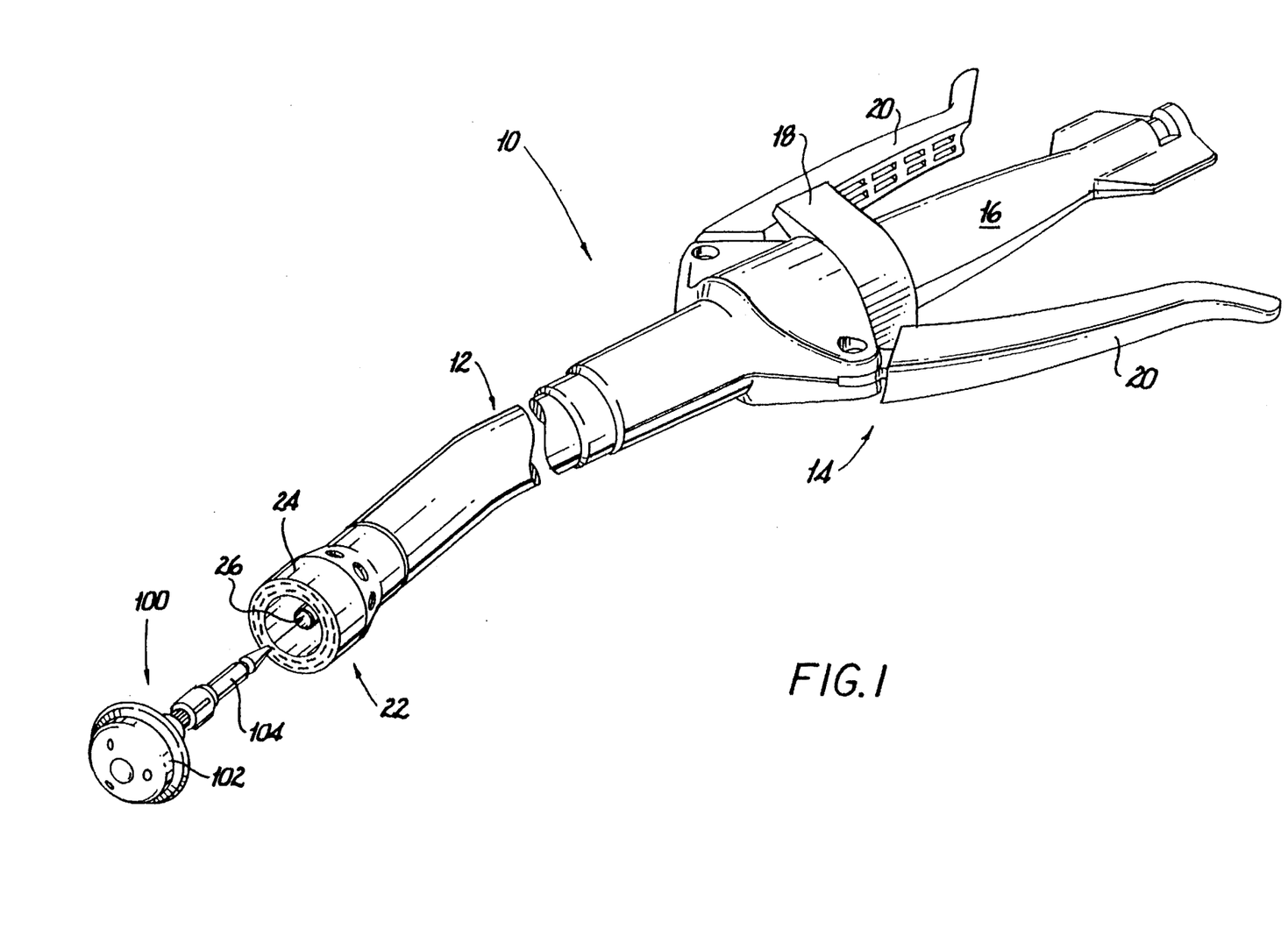
FIG. 1 is a perspective view of a surgical stapling instrument and pivotable anvil assembly suitable for use therewith.
Figure 2:
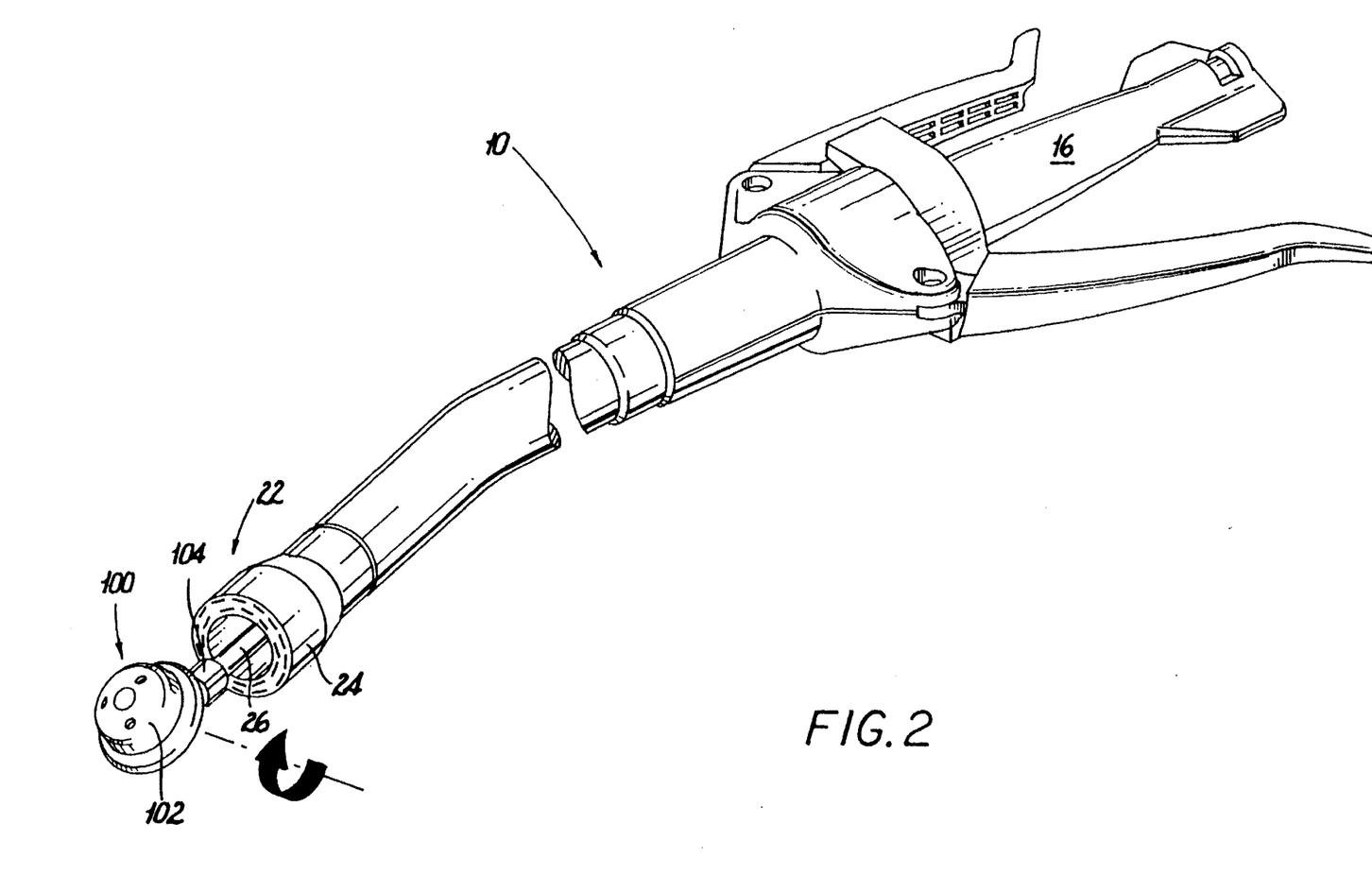
FIG. 2 is a view similar to that of FIG. 1 with the anvil pivoted relative to the anvil shaft.
Figure 6:
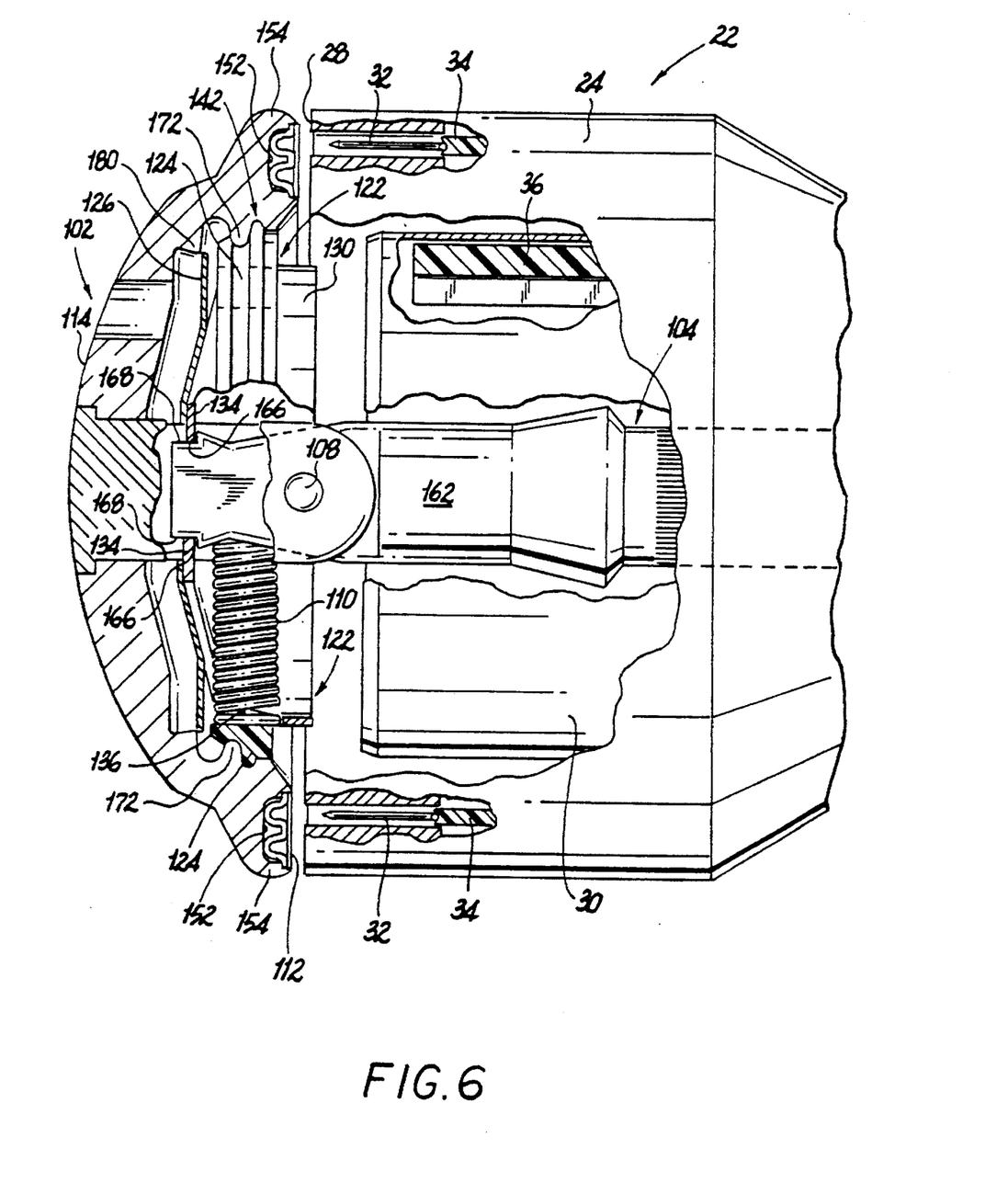
FIG. 6 is a partial cut-away elevational view of a preferred embodiment of the pivotable anvil assembly and distal head portion of a circular stapler wherein the anvil is disposed adjacent the tissue contacting surface portion of the circular stapler.

Referring now in specific detail to the drawings, in which like reference numerals identify similar or identical elements throughout the several views, and initially to FIG. 1, which shows a surgical instrument 10 for applying a circular array of fasteners, e.g., staples, instrument 10 includes elongate body portion 12, proximal handle section 14 and distal fastener head portion 22. Throughout this description, the term "proximal" refers to the end of the apparatus closest to the operator, while the term "distal" refers to the end furthest from the operator. Handle section 14 includes anvil adjustment member 16, lever lockout or safety member 18 and fastener firing levee 20. Fastener head portion 22 includes annular staple cartridge 24 and movable anvil shaft connecting member 26. Anvil shaft connecting member 26 is longitudinally movable between a first, extended position (FIG. 2) and a second, retracted position (FIGS. 1 and 6). In FIG. 1, pivotable anvil assembly 100 is shown spaced from fastener head portion 22 and includes anvil 102 secured to a distal portion of shaft 104. The proximal portion of shaft 102 is adapted to be secured to anvil shaft connecting member 26 (FIG. 2).

The overall operation of fastening device 10 is well known in the art and described in several patents, such as commonly assigned U.S. Pat. Nos. 4,576,167, 5,005,749, and 5,119,983. Except where noted otherwise, the materials utilized in the components of the surgical instrument generally include such materials as polycarbonate for housing sections and related components, and stainless steel for the anvil assembly and components which transmit forces. However, equivalent alternative materials will readily come to the mind of those skilled in the art.

Figure 3:
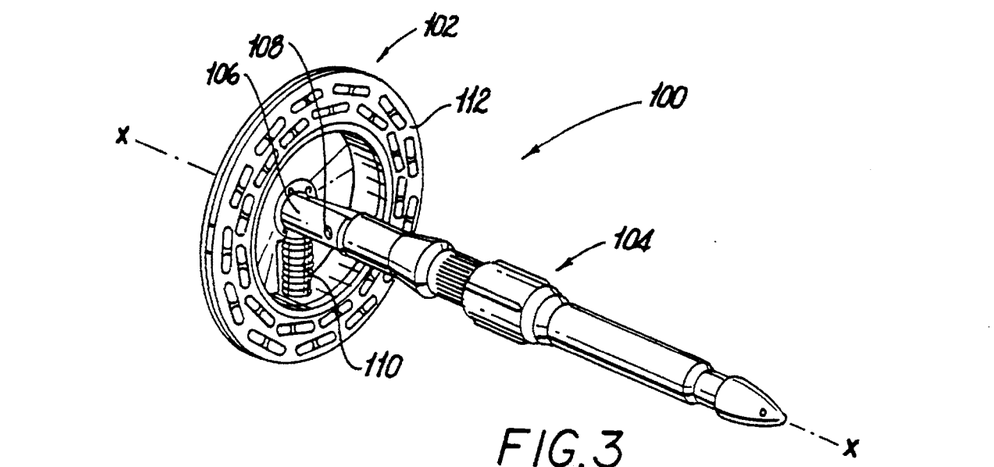
FIG. 3 is a perspective view of a pivotable anvil assembly in accordance with a preferred embodiment of the present invention.
Figure 4:
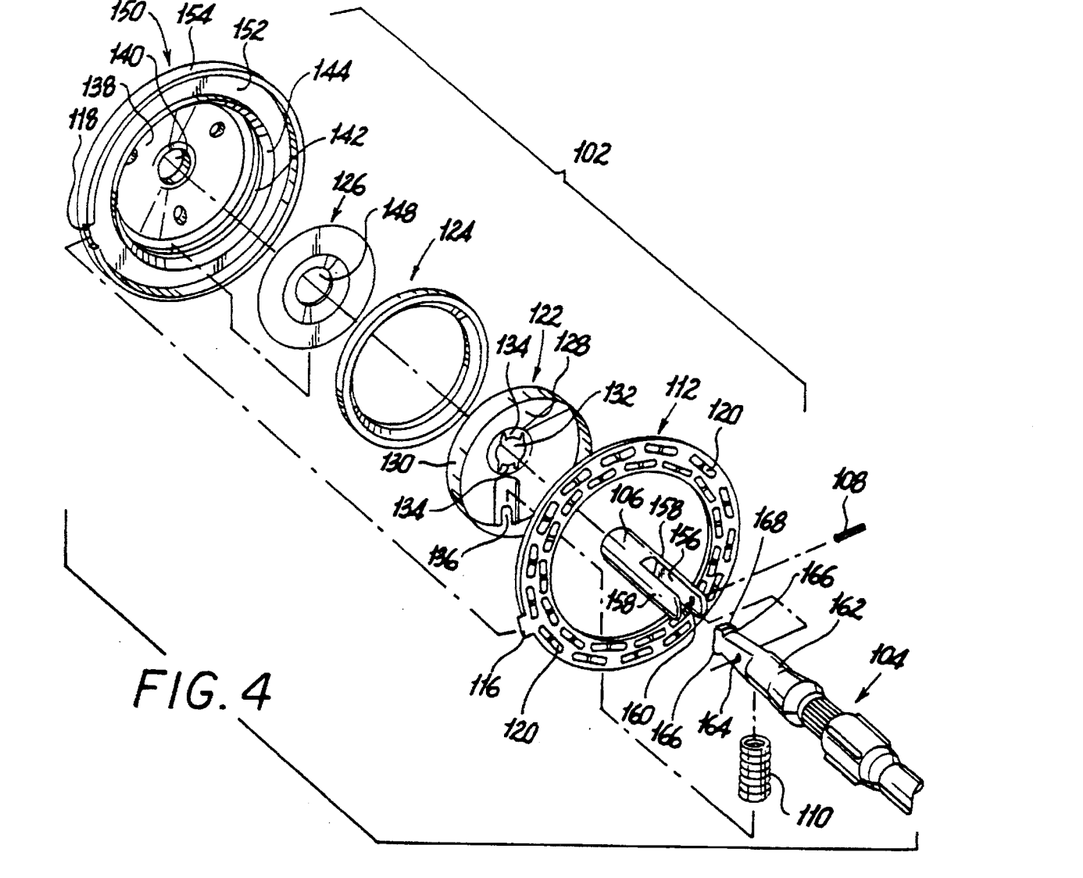
FIG. 4 is an exploded perspective view of the anvil assembly of FIG. 3.

Referring now to FIGS. 3 and 4, various components of the pivoting anvil assembly 100 are shown in detail, In FIG. 3, anvil shaft 104 extends proximally and substantially perpendicular from a plane defined by staple forming surface 112 of anvil 102. Anvil 102 includes post member 106 which extends proximally and substantially perpendicular from a central portion of anvil 102. When longitudinally aligned, both post 106 and shaft 104 extend along a common longitudinal axis X—X which preferably passes through a central portion of anvil 102. The distal portion of shaft 104 is pivotally secured to post member 106 by pivot pin 108. Other structures that permit pivotal movement are also contemplated, i.e., hinges. Spring member 110 is disposed between the distal portion of shaft 104 and anvil 102, the purpose of which is described in greater detail, below.

With reference to FIG. 4, staple forming surface 112 is positioned on a proximal side of anvil housing 150 of anvil 102 and secured thereto by any suitable means. Preferably, surface 112 is pre-stamped and provided with at least one key 116 which mates with corresponding key slots 118 in rim 154 of the anvil housing. Key 116 ensures proper alignment of staple buckets 120 with staples ejected from the instrument (see FIGS. 6–9). Anvil 102 further includes retaining member 122, cut ring 124 and resilient member 126, all of which are preferably disposed radially within staple forming surface 112. Retaining member 122 includes backplate 128, rim 130 projecting proximally from backplate 128 and central orifice 132 into which projections 134 protrude. Rim 130 has tang 136 which projects towards a central portion of retaining member 122 and serves w at least partially retain spring 110, as best seen in FIG. 6. When the anvil is oriented as shown in FIGS. 3 and 6, spring 110 is compressed with one end contacting the distal end of anvil shaft 104 and the other end surrounding tang 136 and contacting rim 130 of retaining member 122.

Figure 5:
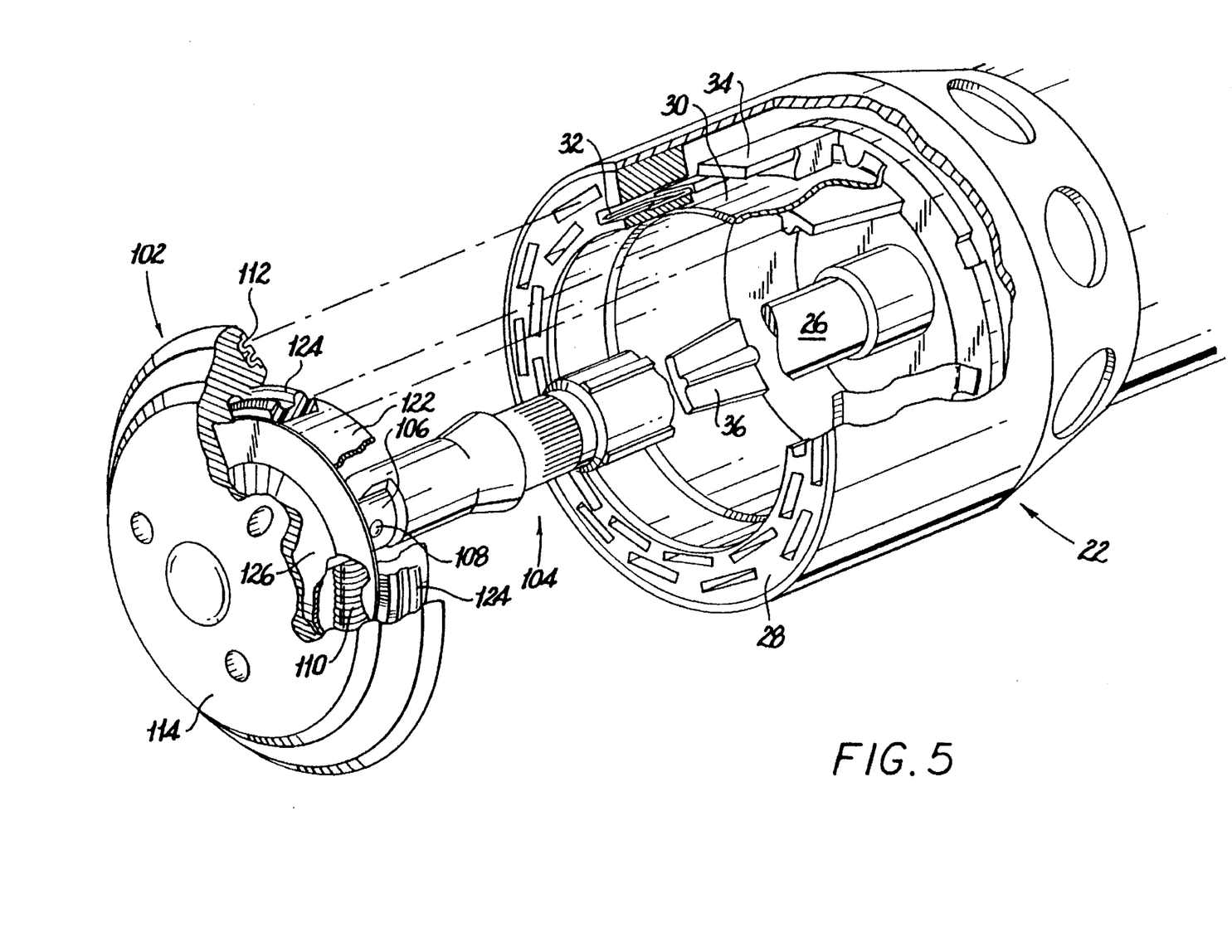
FIG. 5 is a partial cut-away perspective view of the pivotable anvil assembly of FIG. 3 in relation to the distal head portion of a circular stapler.

Anvil housing 150 includes distal domed or convex surface portion 114 (see FIG. 5) proximal inner surface portion 138, in which orifice 140 is centrally disposed, wall 142, sloped surface 144, ledge 152 and rim 154. When assembled, resilient member 126 is disposed between retaining member 122 and proximal surface portion 138, cut ring 124 is disposed between wall 142 and retaining member 122 and staple forming surface 112 is disposed adjacent ledge 152. Preferably, the proximal surface fortion of cut ring 124 is disposed adjacent or distal the distal-most portion of sloped surface 144 (see also FIG. 6).

Resilient member 126 serves to bias retaining member 122 in a proximal direction and to provide tactile and/or audible feedback during firing (see below). If such feedback is not desired, resilient member 126 can be eliminated from anvil 102 and retaining member 122 can be frictionally maintained within anvil housing 150 and still perform it's stated function as described below.

Turning to the securement of anvil shaft 104 to anvil 102, with reference to FIGS. 3, 4 and 6, anvil shaft 104 has a distal portion 162 which includes hole 164 through which pin 108 passes. Post member 106 is secured to anvil backplate 138 at orifice 140 by any suitable means, such as screw fit, welding, glue and the like, and projects substantially perpendicular to and proximally from housing 150. Alternatively, post member 106 and housing 150 can be formed as a single, integral part. Post member 106 preferably has slot 156 defined between parallel arms 158. Arms 158 each have holes 160 through which pin 108 passes to pivotally secure distal portion 162 of anvil shaft 104. The distal end of shaft distal portion 162 has flat ledges 168 against which projections 134 of retaining member 122 rest when the anvil and shaft are in the locked position (see FIG. 6). In the locked position, retaining member 122 holds shaft 104 in a substantially perpendicular position with respect to anvil 102, thereby preventing rotation of shaft 104 (or anvil 102, depending on the frame of reference) about pin 108. Preferably, as shown, projections 134 of retaining member 122 contact distal shaft portion 162. Of course, one skilled in the art could modify retaining member 122 to provide other structures that prevent rotation of the anvil relative to the shaft. Such modifications are considered within the scope of the present invention. Also shown in FIG. 6, resilient member 126 holds retaining member 122 in place by biasing the retainer proximally against protrusions 166 on distal shaft portion 162. The periphery of resilient member 126 contacts wall 142 of housing 150 at ledge 180.

The relationship of anvil assembly 100 with respect to fastener head portion 22 is illustrated in FIGS. 5–9. With anvil 102 locked into perpendicular alignment with shaft 104, the proximal end of shaft 104 is oriented towards fastener head 22 such that staple forming surface 112 of anvil 102 is facing tissue contacting surface 28 of fastener head 22. As is known in the art, moving anvil assembly 100 proximally, the proximal portion of shaft 104 can be inserted longitudinally into the hollow, distal end portion of anvil shaft connecting member 26 (see FIGS. 1 and 2) to releasably mount the anvil shaft to the anvil shaft connecting member. See, e.g., U.S. Pat. No. 5,119,983. Once connected, anvil assembly 100 can be moved proximal and/or distal with respect to fastener assembly 22 by rotating anvil adjustment member 16.

Turning to FIGS. 6–9, operation of the surgical stapling apparatus is illustrated. For purposes of clarity, tissue structure is not shown. In FIG. 6, anvil adjustment member 16 (FIG. 1) has been rotated to bring anvil 102 into close approximation with fastener head portion 22. In this pre-fired condition, knife 30, release pushers 36, staple pushers 34 and staples 32 are all positioned proximal of tissue contacting surface 28. Shaft 104 is in its locked position wherein projections 134 of retaining member 122 are in contact with ledges 168 of the distal end of anvil shaft 104. In the locked position, shaft 104 is in substantially perpendicular alignment with respect to anvil 102 and spring 110 is compressed and prevented from moving and/or biasing the anvil relative to the shaft.

Figure 7:
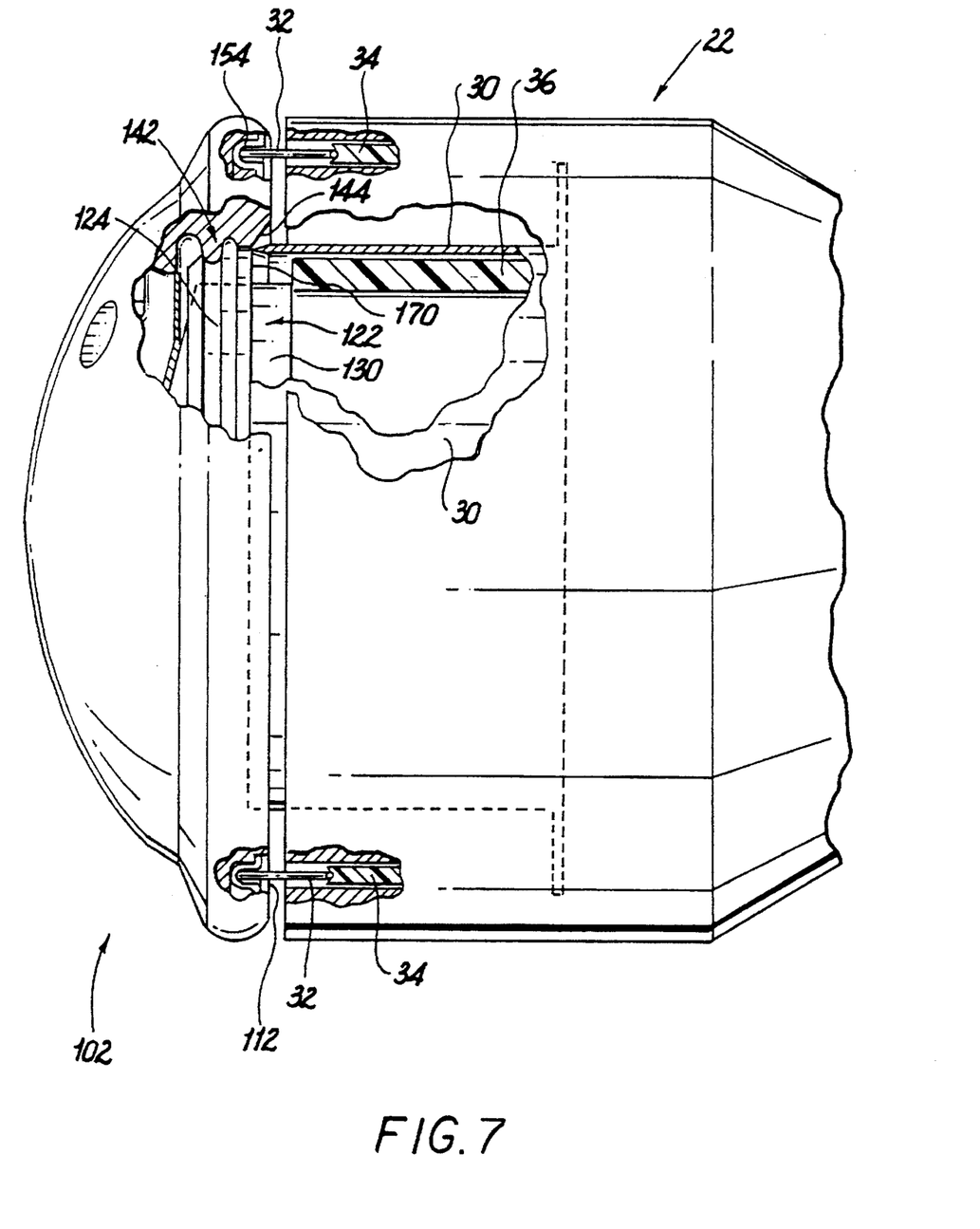
FIG. 7 is a view similar to that of FIG. 6 wherein the surgical stapling apparatus has been partially actuated.

Turning to FIG. 7, firing of the instrument has commenced by squeezing fastener firing levers 20 (FIG. 1), as is known in the art. Movement of levers 20 cause staple pushers 34 to move distally, thereby ejecting staples 32 past the plane defined by tissue contacting surface 28, through tissue (not shown) disposed between tissue contacting surface 28 and staple forming surface 112, and into contact with staple buckets 120 of staple forming surface 112. Also advancing distally during firing are knife member 30 and release pushers 36 which are preferably disposed inside the periphery of the circular knife. In this stage of advancement, distal movement of the firing mechanism has brought release pushers 36 into contact with rim 130 of retaining member 122 and the distal cutting portion of knife 30 into contact with the proximal surface portion 170 of cut ring 124. While release pushers 36 are shown inside circular knife 30, other structures, including knife 30, can be adapted to move retaining member 122 during firing. Also shown in FIG. 7, had knife 30 been slightly off-center, sloped surface 144 would guide the knife back into alignment.

Figure 8:
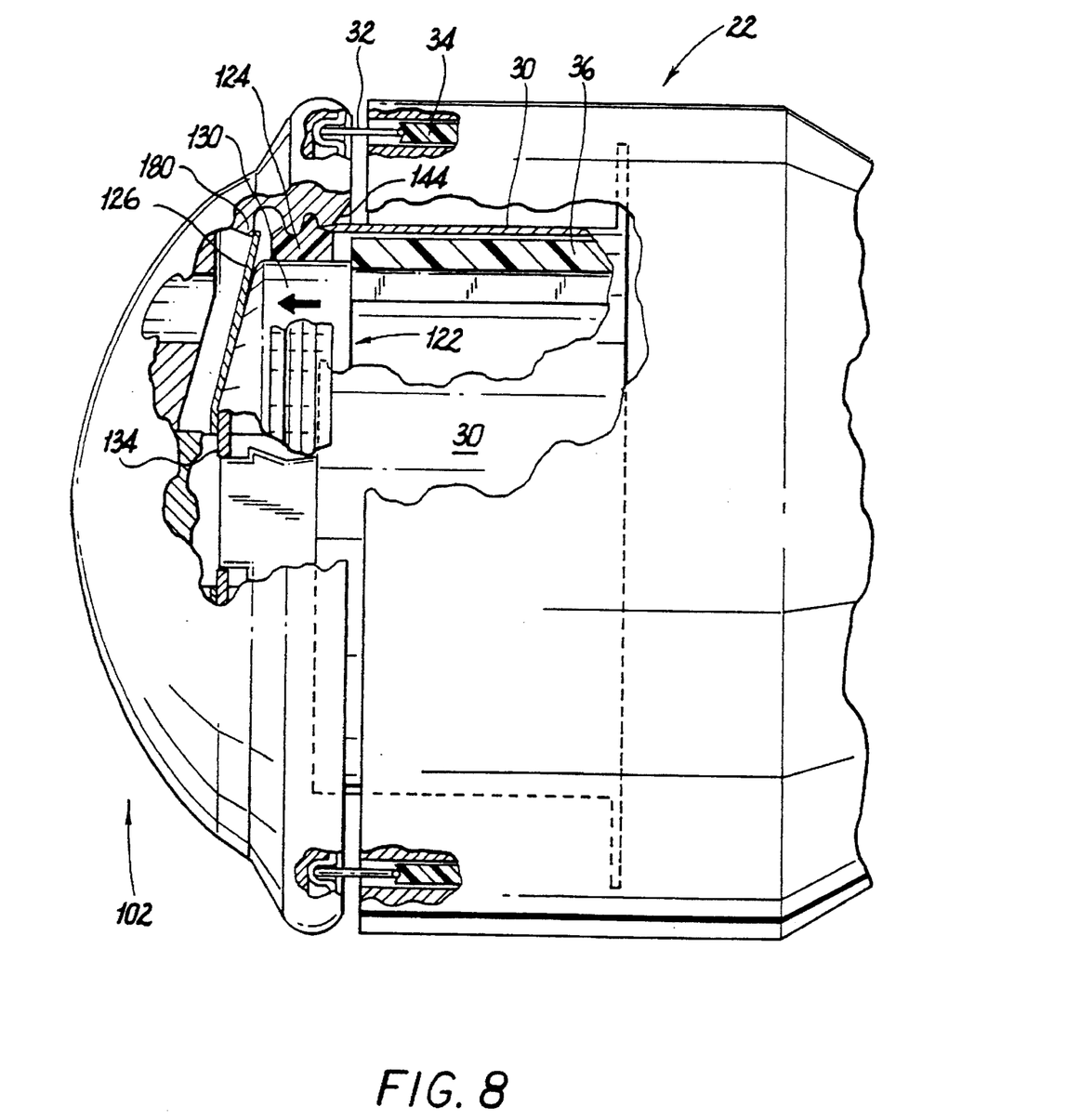
FIG. 8 is a view similar to that of FIG. 7 showing further actuation of the surgical stapler.

Further movement of the firing mechanism, as shown in FIG. 8, shows staples 132 forming against staple forming surface 112, knife 30 penetrating cut ring 124 (to cut tissue disposed between tissue contacting surface 28 and staple forming surface 112) and release pushers 36 pushing retaining member 122 in a distal direction (see arrow). As shown, projections 134 of retaining member 122 have also moved in a distal direction, but have not released from ledges 168 of shaft 104. Resilient member 126 has also started to deflect, but remains in contact with ledge 180 of anvil housing 150.

Figure 9:
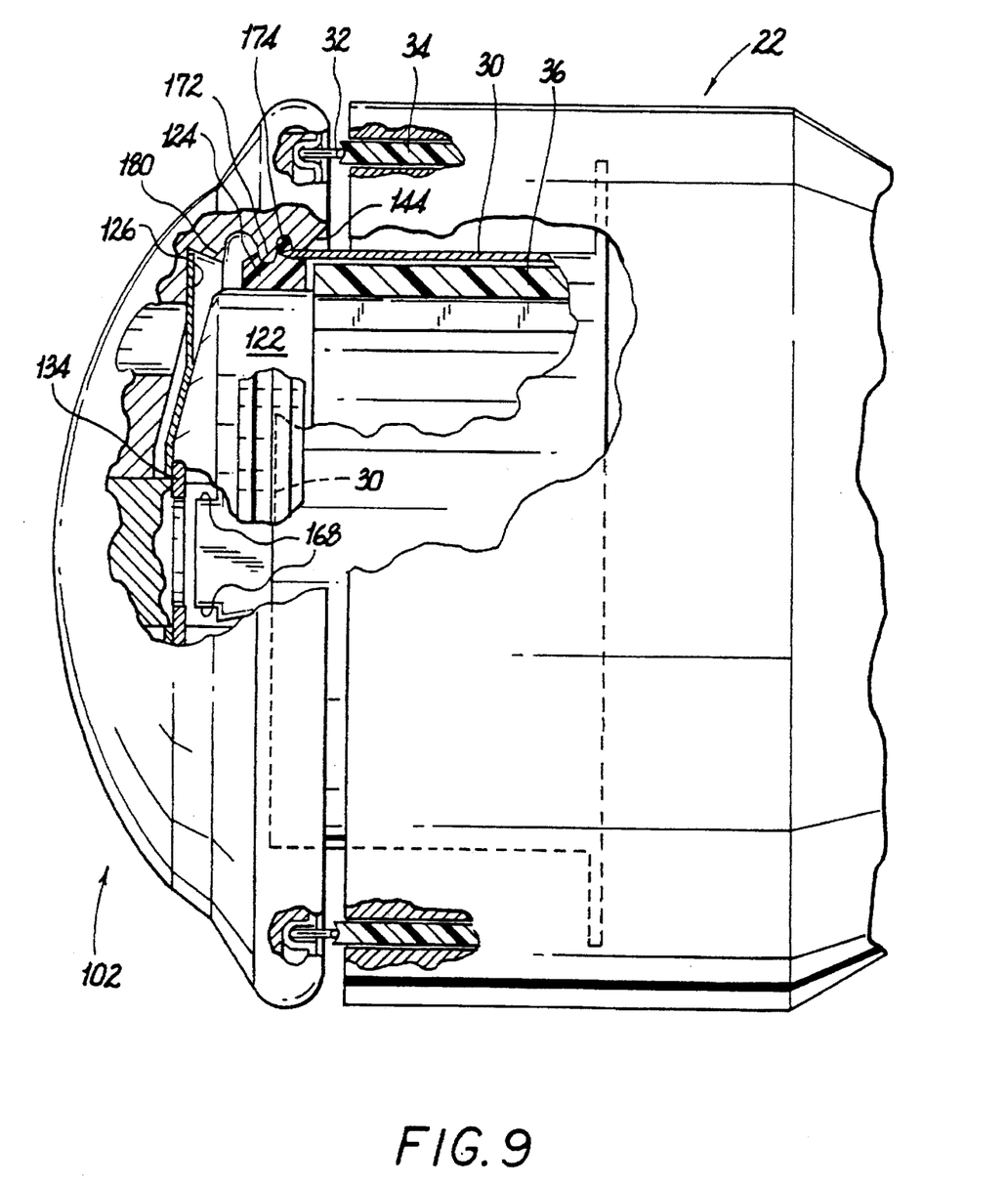
FIG. 9 is a view similar to that of FIG. 8 wherein the surgical stapler has completed the firing stroke.

FIG. 9 illustrates the state of the surgical apparatus after completion of the firing stroke. In this position, staples 32 are fully formed against staple forming surface 112, staple pushers 34 extend partially distal of tissue contacting surface 28, and the distal end of knife 30 has bottomed out against circular knife contacting surface 174 of shelf 172 extending from anvil wall 142. Release pushers 36 have pushed retaining member 122 a sufficient distance so that projections 134 are disengaged with the distal end of shaft 104. In this position, anvil 102 is now free to route with respect to anvil shaft 104, however, fastener head portion 22 prevents such rotation while anvil 102 is adjacent thereto. Resilient member 126 has been forced off ledge 180 and is at least partially disposed against proximal surface 138 of anvil housing 150. The action of resilient member 126 being forced off ledge 180 causes an audible and/or tactile event that can be sensed by the surgeon. Though optional, such an event is useful to indicate completion of the firing stroke.

Figure 10:
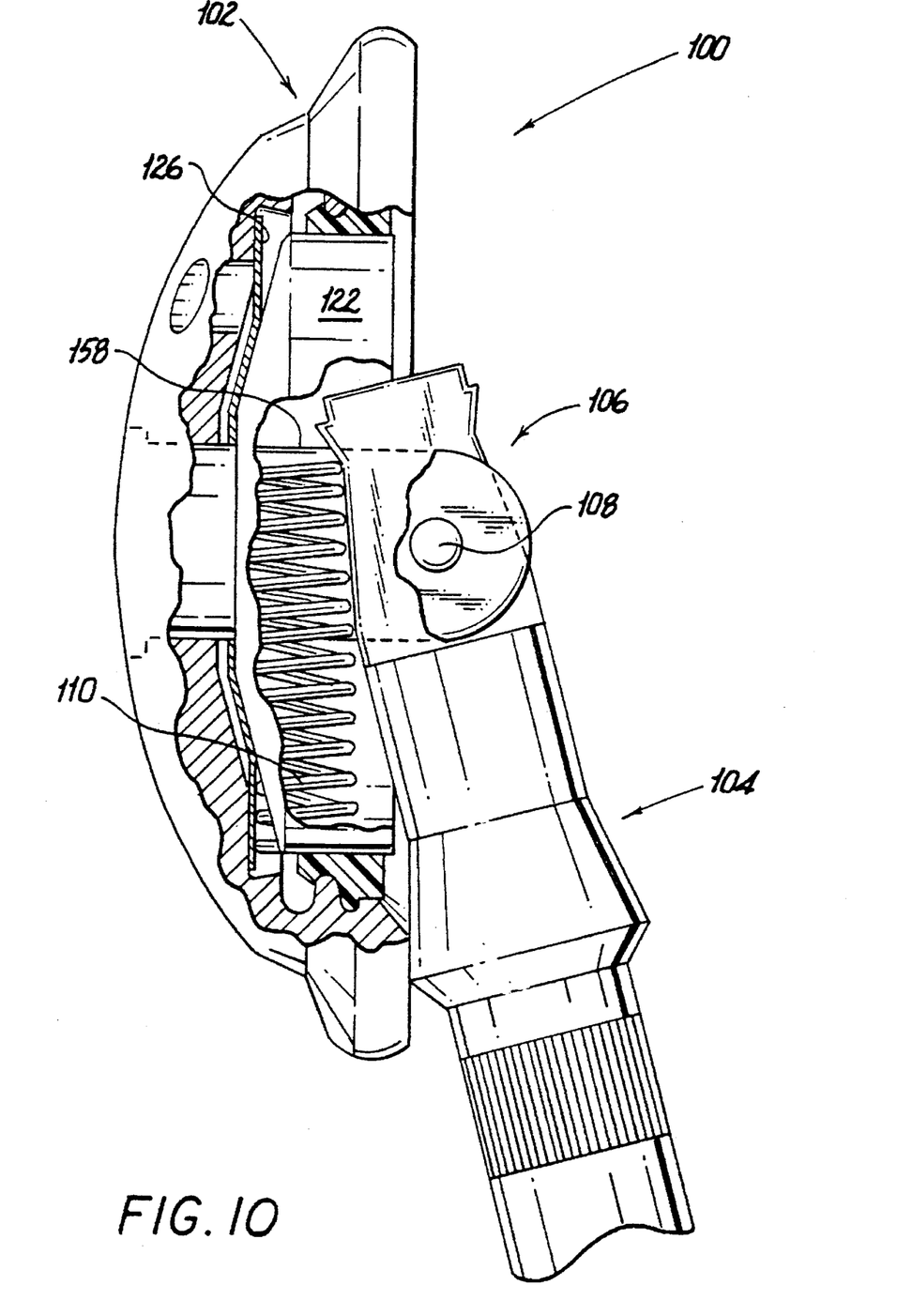
FIG. 10 is a partial cut-away elevational view of the pivotable anvil assembly with the anvil pivoted relative to the anvil shaft.

With reference to FIGS. 2 and 10, after firing, anvil adjustment member 16 can be rotated to move anvil assembly 100 away from fastener head portion 22. Upon sufficient distal movement of the assembly, spring 110 pivotally biases anvil 102 relative to anvil shaft 104. Pivoting or tilting occurs as spring 110 expands and forces the distal end of anvil shaft 104 out from between arms 158 of post 106. The biasing action causes post 106 to pivot about pin 108. When anvil 102 is biased, it moves from a first position, wherein the plane deemed by staple forming surface 112 is substantially perpendicular to the longitudinal axis of anvil shaft 104, to a second position, wherein the staple forming surface plane is off-set from the first position. In the tilted position, a lower profile is presented than in the non-titled position and the instrument is readily withdrawn through the anastomotic site. While it is preferable to have a biasing member to facilitate tilting, tilting can also occur upon removal without a biasing member.

Figures 11, 12:
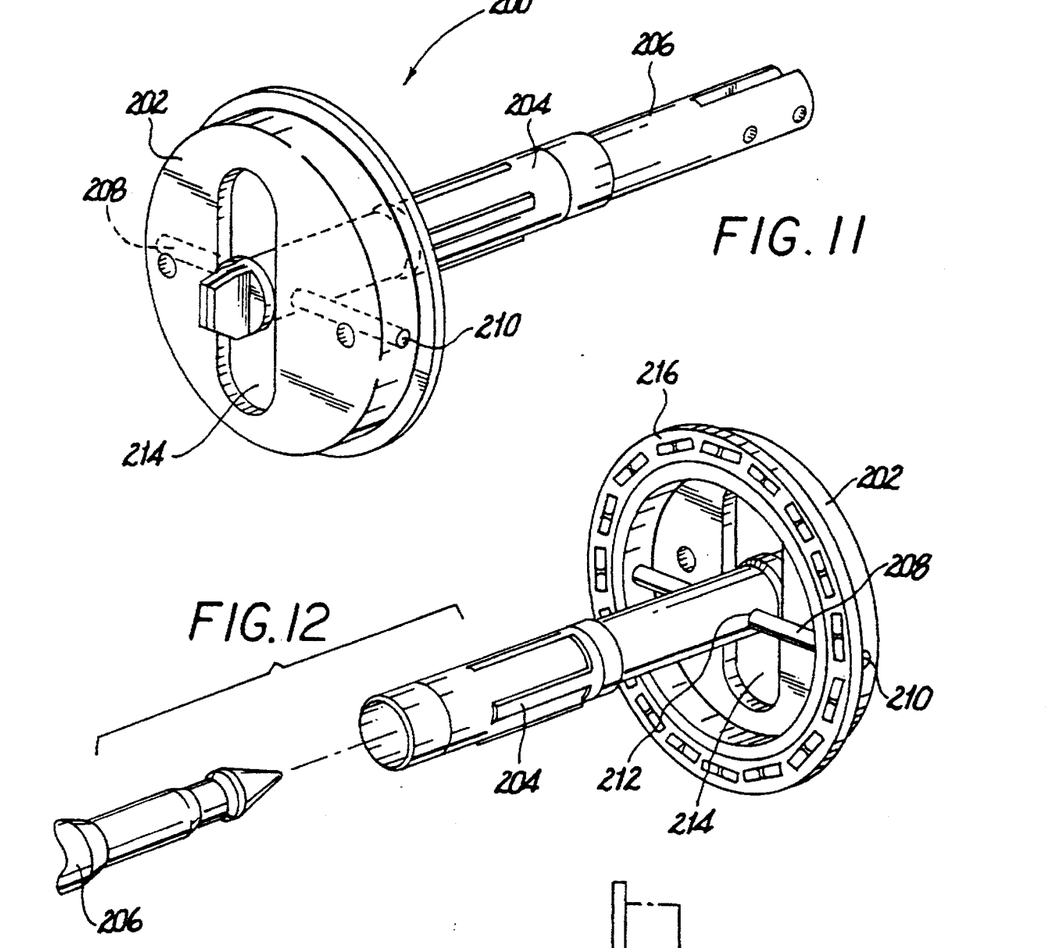
FIG. 11 is a perspective view of an alternative embodiment of a pivotable anvil assembly.
FIG. 12 is a view similar to that of FIG. 11 showing proximal orientation of the pivotable anvil assembly.
Figure 13:
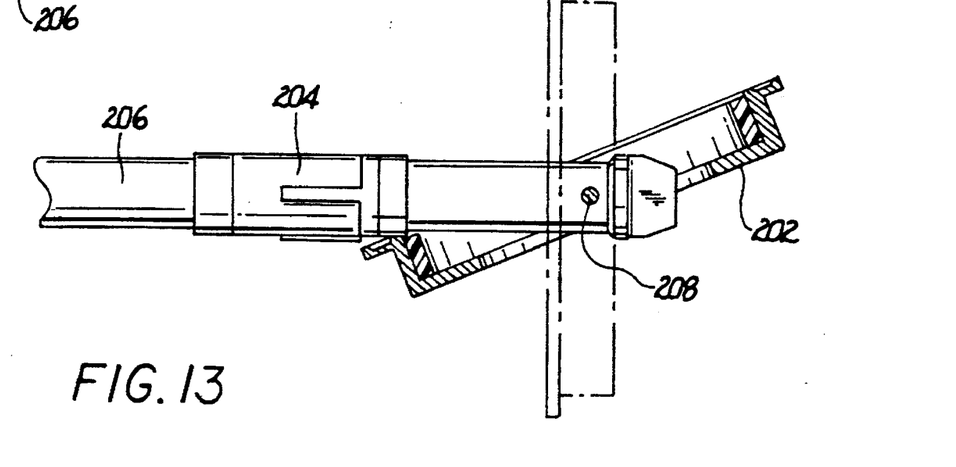
FIG. 13 is a side elevational view of the pivotable anvil assembly of FIG. 12 showing relative movement of the anvil and anvil shaft.

Turning to FIGS. 11–13, an alternate embodiment of a tilting anvil assembly is shown. In this embodiment, the anvil shaft is a substantially hollow cylinder and the anvil connecting portion of the stapler is solid. Such structure, which is equivalent to a solid anvil shaft engaging a hollow anvil securement potion, is disclosed in U.S. Pat. No. 5,205,459. Anvil assembly 200 includes anvil 202 and shaft 204. Shaft 204 is hollow as opposed to shaft of 104 of the previous embodiments which is preferably solid. Shaft 204 is configured and dimensioned to receive trocar 206 which functions in a manner similar to anvil connecting member 26 (previous embodiments). Pin 208 seems shaft 204 to anvil 202 by passing through orifices 210 and bore 212 in anvil head 202 and the distal end portion of shaft 204, respectively. Slot 214 is provided in the distal housing portion of anvil 202 to permit clearance for the end of shaft 204 during rotation. Slot 214 can be eliminated by having shaft 204 pivot at a more proximal location. Although not shown, structures equivalent to the biasing and retaining members described above can be used to retain anvil 202 in a locked, perpendicular position with respect to shaft 204 and release upon firing.

Returning to cut ring 124 and FIGS. 6–9, the cut ring disclosed provides several advantages over the prior art. As set forth in the background section of this disclosure, during performance of an anastomosis, both tissue and staples may need to be severed by the knife. It is known that by providing a semi-rigid cut ring, (see, for example, commonly assigned U.S. Pat. Nos. 4,304,236, 4,505,272 and 5,119,983), tissue is easily severed. However, when metallic staples (i.e., titanium or stainless steel staples) are disposed in the path of the knife, the staples tend to bend and deform against the semi-rigid cut ring. Deformed/uncut staples can join tissue and other structures within and without the circular cut. Structures that improve cutting, as illustrated in FIGS. 6–9, include cut ring 124 and ledge 172. Ledge 172 protrudes from inner wall portion 142 of anvil 102 and into the path of knife blade 30. Proximal surface 174 of ledge 172 provides a knife contacting surface against which knife 30 contacts at the end of the firing stroke. Preferably, the knife contacting surface assumes a geometry similar to that of the distal cutting surface of the knife blade. In this particular embodiment, the knife blade is circular and, therefore, ledge 172 and knife contacting surface 174 are also circular. While ledge 172 and knife contacting surface 174 are preferably metallic, any rigid surface which permits cutting of metal staples is suitable for use. Other suitable materials can include, for example, ceramic, rigid plastics or other sufficiently hard man-made or naturally occurring rigid substances. In operation, distal movement of knife blade 30 will initially sever tissue as the knife blade passes through cut ring 124. Further distal movement will sever staples, if present, against surface 174. Since ledge 172 is fabricated from a rigid material, further movement of knife 30 is prevented due to contact with surface 174.

Figure 14:
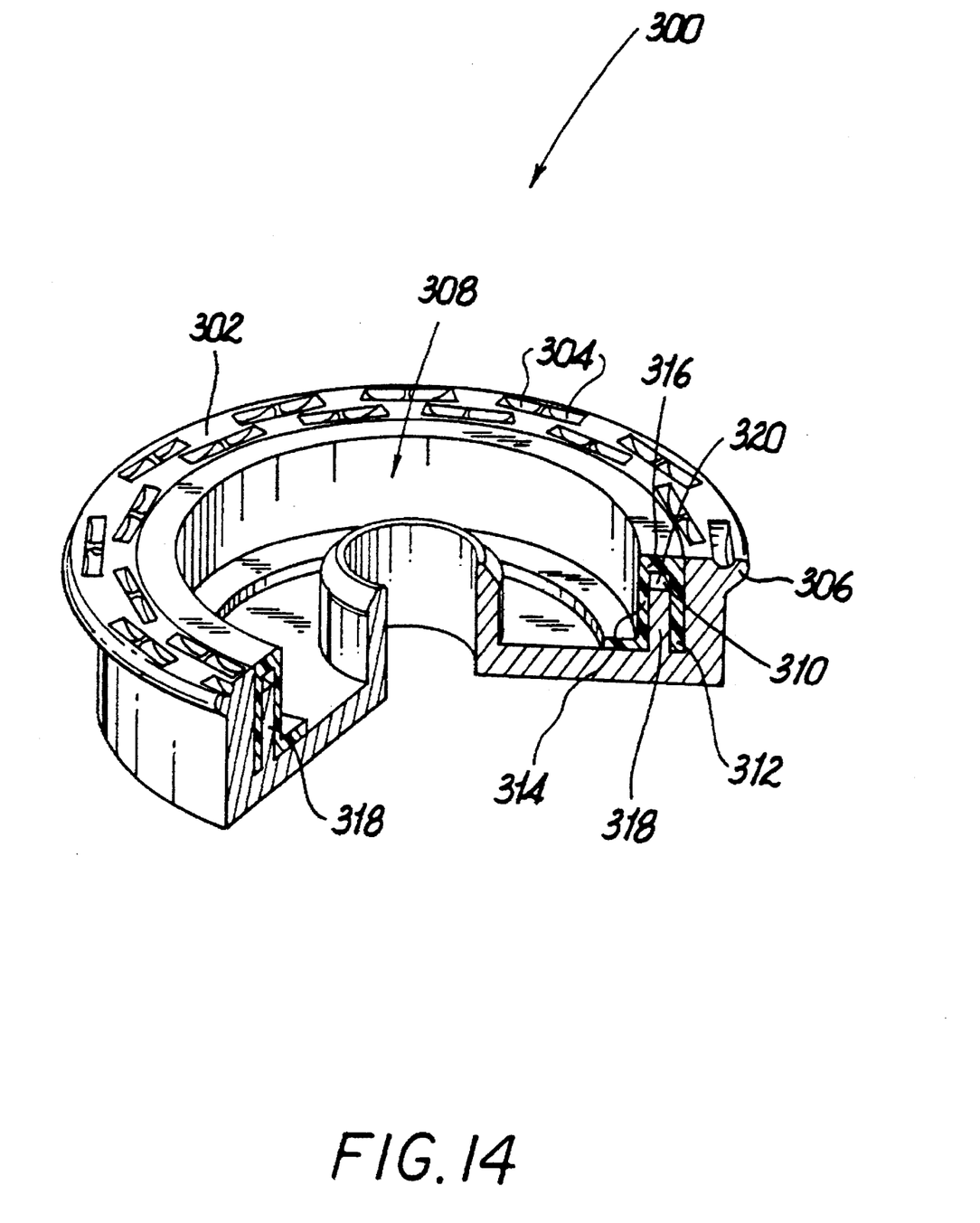
FIG. 14 is an alternative embodiment of an anvil for a surgical stapler having structure particularly adapted for cutting tissue and staple material in the path of a knife blade.

The cutting surface concept shown in FIGS. 6–9 can also be applied to anvil 300 shown in FIG. 14. Anvil 300 is similar to that disclosed in U.S. Pat. No. 5,205,459. Anvil 300 has annular rim 306, staple forming surface 302, and staple forming buckets 304. Within annular rim 306, semi-rigid cut ring or "backup washer" 308 is mounted within the anvil to provide a tissue ending surface. Backup washer 308 is annular in configuration and is mounted concentrically inside rim 306. An annular groove 310 extends inwardly into washer 308 from its distal end and terminates short of its proximal end. As a result of groove 310, washer 308 has an outer annular wall 312 and an inner annular wall 314 joined by a thin web 316 at the proximal end of the washer. An improvement to this known anvil and cut ring is the provision of protrusion or wall 318 which has proximal knife contacting surface 320. Wall 318 projects into annular groove 310 and preferably terminates distal of web 316. In use, when a knife member is advanced toward cut ring 308, the knife will initially contact and cut tissue against upper surface or web portion 316 of washer 308. Further movement of the knife will cause the knife to pass through web 316 and to contact with surface 320 to cut of staples against rigid surface 320. The space between surface 320 and web 316 allows for tactile feedback to the user upon cutting web 316. Of course, it also is contemplated that wall 318 can project sufficiently into groove 310 so that surface 320 is directly adjacent web 316.

It will be understood that various modifications may be made to the embodiments disclosed herein. For example, while the application is primarily related to circle stapling instruments, the pivoting/tilting anvils can also be adapted for use with non-stapling circular anastomosis instruments. Such instruments are disclosed, for example, in commonly assigned U.S. Pat. Nos. 4,917,114, 4,931,057, 4,966,682, 5,122,156. In addition, the advantage of providing a tilting anvil assembly for purposes of removing the surgical instrument after firing can be applied to pre-firing insertion of the instrument wherein the anvil can be tilted prior to insertion into an organ, untilted for firing (i.e., brought into perpendicular alignment with the anvil shaft) and then tilted for withdrawal. Also, the tilting anvil can be used with or without the novel cut ring embodiment, and vice versa. It is also not necessary that the anvil shaft be detachable from the instrument Therefore, the above description should not be construed as limiting but merely as exemplification of preferred embodiments. Those skilled in the art will envision other modifications within the scope and spirit of the claims appended hereto.

As used in the claims, "biasing means" is intended to refer to spring member 110 and equivalents thereof.

As used in the elm, "locking means" is intended to refer to retaining member 122 and equivalents thereof.

What is claimed is:

1. In an anvil assembly for a circular stapling instrument, the anvil assembly having an anvil member with an annular staple forming surface and an annular array of staple forming buckets formed in the staple forming surface, and a shaft having a longitudinal axis extending from the anvil member in a direction substantially perpendicular with respect to the staple forming surface, the improvement comprising:

a sloped annular surface portion disposed adjacent to and radially inward of the staple forming surface, the sloped annular surface portion sloping radially inwardly and distally from the staple forming surface.

2. The anvil assembly according to claim 1, wherein the shaft is solid.

3. The anvil assembly according to claim 1, wherein the shaft is hollow.

* * * * *